US010892060B1

(12) United States Patent
Silverstein et al.

(10) Patent No.: US 10,892,060 B1
(45) Date of Patent: Jan. 12, 2021

(54) SYSTEM AND METHOD FOR PROVIDING NOTIFICATIONS TO A USER BASED UPON THE LOCATION OF THE USER

(71) Applicant: Amaze PBC, Denver, CO (US)

(72) Inventors: David Mark Silverstein, Longmont, CO (US); Felix Weitzman, Conifer, CO (US)

(73) Assignee: Amaze PBC, Denver, CO (US)

(*) Notice: Subject to any disclaimer, the term of this patent is extended or adjusted under 35 U.S.C. 154(b) by 0 days.

(21) Appl. No.: 16/684,565

(22) Filed: Nov. 14, 2019

(51) Int. Cl.
*H04W 4/021* (2018.01)
*G16H 80/00* (2018.01)
*H04W 68/00* (2009.01)

(52) U.S. Cl.
CPC ........... *G16H 80/00* (2018.01); *H04W 4/021* (2013.01); *H04W 68/005* (2013.01)

(58) Field of Classification Search
CPC ....... H04W 4/02; H04W 4/021; H04W 4/024; H04W 4/12; H04W 4/029; H04W 4/08; H04W 4/33; H04W 68/00; H04W 76/50; G16H 40/20; G16H 40/67; G16H 10/60
See application file for complete search history.

(56) References Cited

U.S. PATENT DOCUMENTS

| | | | |
|---|---|---|---|
| 7,925,519 B2 | 4/2011 | Greene et al. | |
| 8,010,717 B2 | 8/2011 | Evans et al. | |
| 8,504,386 B2 | 8/2013 | Manning et al. | |
| 8,554,195 B2 | 10/2013 | Rao | |
| 8,600,008 B2 | 12/2013 | Kraus et al. | |
| 8,924,238 B1 | 12/2014 | Niddy et al. | |
| 9,886,547 B2 | 2/2018 | Baniameri et al. | |
| 9,924,315 B1 | 3/2018 | Cornwall et al. | |
| 10,178,537 B2 | 1/2019 | Rauner | |
| 10,492,023 B1 * | 11/2019 | Gurin | H04W 4/029 |
| 2018/0089387 A1 | 3/2018 | Swank | |
| 2018/0166176 A1 * | 6/2018 | Flippen | A61B 5/7465 |
| 2019/0043613 A1 * | 2/2019 | Gallagher | G08B 25/10 |
| 2019/0088106 A1 | 3/2019 | Grundstrom | |
| 2019/0237187 A1 | 8/2019 | Carter et al. | |

* cited by examiner

Primary Examiner — Jean A Gelin
(74) Attorney, Agent, or Firm — Brett A. Schenck

(57) ABSTRACT

This application provides a computer-implemented method for providing notifications. The method includes a) creating a geofenced area associated with a mobile device and a healthcare facility, wherein the patient is associated with the mobile device, b) storing the geofenced area in a data store, c) determining when the mobile device has crossed or entered the geofenced area during an unscheduled visit to the healthcare facility by the patient, d) sending a notification to or retrieving the notification from the mobile device, wherein the notification includes the medical history of the patient, the type of healthcare facility associated with the geofenced area, the insurance network of the patient, the medical providers practicing at the healthcare facility, wait times at the healthcare facility, and the proximity to other healthcare facilities, and e) outputting the notification to the mobile device when mobile device is within the geofenced area.

20 Claims, 7 Drawing Sheets

SYSTEM AND METHOD FOR PROVIDING NOTIFICATIONS TO A USER BASED UPON THE LOCATION OF THE USER

FIELD

This application relates to a system and method for providing notifications to a user based upon the user's location.

BACKGROUND

Often when a person needs immediate medical attention, he or she may want or need more information related to the medical condition. Sometimes, he or she may want or need more information on the way to the hospital, free-standing emergency room, urgent care center, walk-in clinic or other medical facility so that appropriate decisions can be made. For example, the person may initially be walking into an emergency room, but then determine that the medical condition would be better addressed at an urgent care center or minute clinic instead.

SUMMARY

This application addresses the above-mentioned problem. In one aspect of this application, a computer-implemented method for providing notifications and communication based on a patient entering into a geofenced area around a healthcare services facility for an unscheduled visit is provided. The method includes operations performed by at least one computer processor. These operations include a) creating a geofenced area associated with a mobile device and a location that has the healthcare facility, wherein the patient is associated with the mobile device, b) storing the geofenced area in a data store, c) determining when the mobile device has crossed or entered the geofenced area during the unscheduled visit to the healthcare facility by the patient, d) sending a notification to or retrieving the notification from the mobile device, wherein the notification includes information about one of or any combination of: the medical history of the patient, the type of healthcare facility associated with the geofenced area, the insurance network of the patient, the medical providers practicing at the healthcare facility, wait times at the healthcare facility, and the proximity to other healthcare facilities, wherein the notification further includes an invitation or suggestion to initiate a video or audio call to a qualified person that can help the patient regarding the unscheduled visit, and e) outputting the notification to the mobile device when the location data of the mobile device is determined to be within the geofenced area that corresponds to the healthcare facility.

In another aspect of this application, a computer-implemented method for providing notifications is provided. The method includes operations performed by at least one computer processor. These operations include a) creating a group of geofenced areas, wherein the group of geofenced areas are associated with a mobile device and a location that has a healthcare facility, wherein the patient is associated with the mobile device, b) storing the geofenced areas in a data store, c) determining when the mobile device has crossed or entered at least one of the geofenced areas in the group of geofenced areas, d) sending a notification to or retrieving the notification from the mobile device, wherein the notification includes information about one of or any combination of the medical history of the patient, the type of healthcare facility associated with the geofenced area, the insurance network of the patient, the medical providers practicing at the healthcare facility, wait times at the healthcare facility, and the proximity to other healthcare facilities, and e) outputting the notification to the mobile device when the location data of the mobile device is determined to be within the at least one geofenced area that corresponds to the healthcare facility.

Further embodiments of the disclosed a system and method for providing notifications to a user based upon the user's location will become apparent from the following detailed description, the accompanying drawings and the appended claims.

DETAILED DESCRIPTION

It will be readily understood that the components of the embodiments as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

As used herein, the terms "component" and "system" are intended to encompass hardware, software, or a combination of hardware and software. Thus, for example, a system or component may be a process, a process executing on a processor, or a processor. Additionally, a component or system may be localized on a single device or distributed across several devices.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

Figure 1:
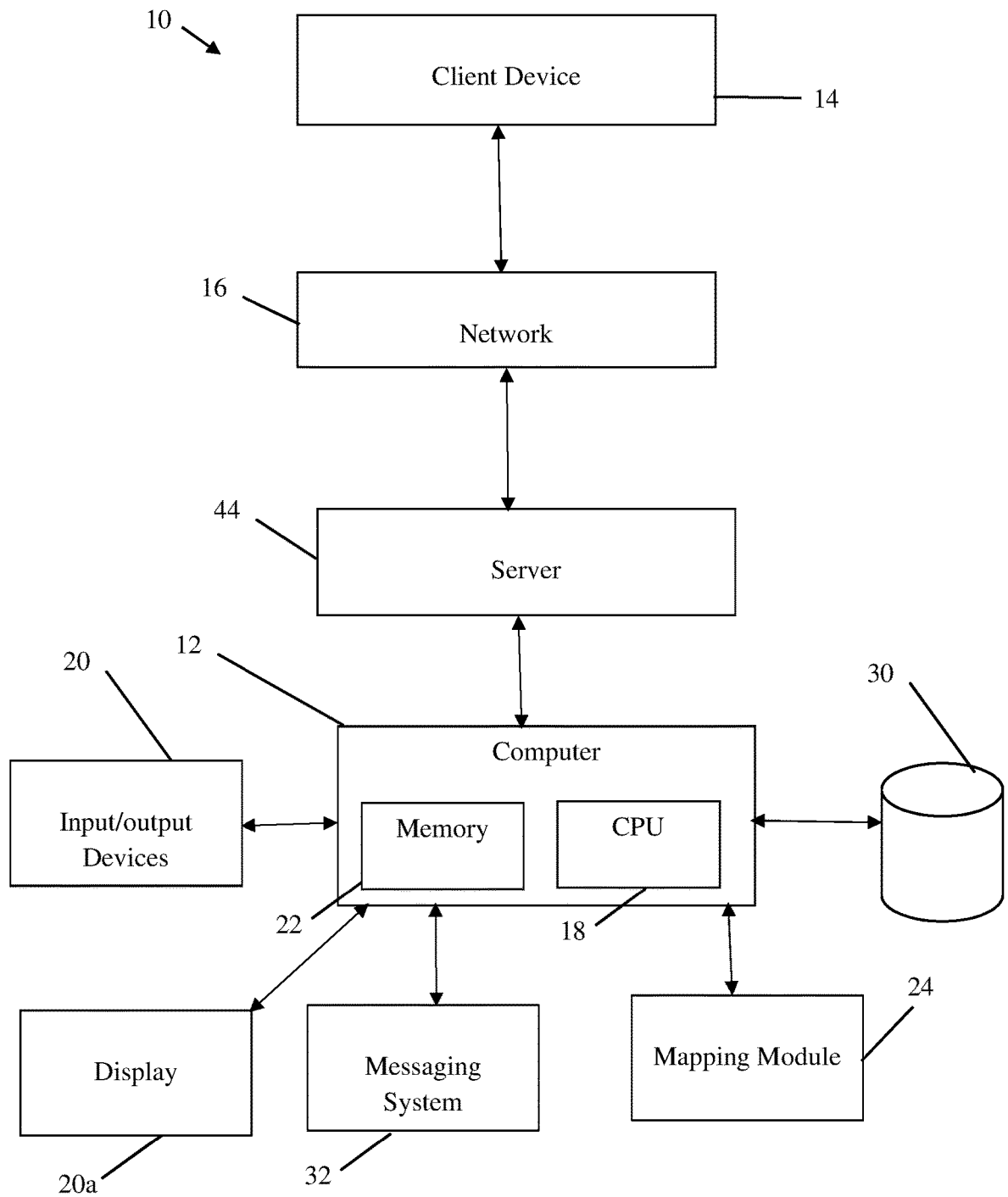
FIG. 1 is a block diagram of the components of the system according to one embodiment of the present invention.

FIG. 1 shows a block diagram of a system 10 that provides notifications to a patient or person as he or she approaches a healthcare facility according to the present invention. The system 10 may include a computer 12 and a client device 14. The components may each be connected and placed in communication with one another over a computer network 16. Embodiments of the network 16 may be constructed using wired or wireless connections between each hardware component connected to the network 16.

The computer 12 may generally comprise a processor 18, otherwise referred to as a central processing unit (CPU), input/output devices 20 such as a display 20a, keyboard, printer etc. coupled to the processor 18, and memory device 22. The processor 18 may perform computations and control the functions of the computer 12, including executing instructions included in the computer code for tools and programs for creating geofenced areas and triggering a geofence notification, in the manner prescribed by the embodiments of the disclosure using the components, wherein the instructions of the computer code may be executed by the processor 18 via memory device 22. The computer code may include software or program instructions that may implement one or more algorithms for implementing the methods for providing a geofence notification. The processor 18 executes the computer code. The processor 18 may include a single processing unit, or may be distributed across one or more processing units in one or more locations (e.g., on a client and server).

The memory device 22 may include input data. The input data includes any inputs required by the computer code. The display 20a displays output from the computer code. The memory device 22 may be used as a computer usable storage medium (or program storage device) having a computer readable program embodied therein and/or having other data stored therein, wherein the computer readable program comprises the computer. The computer 12 may be accessed by a medical professional such as a doctor, physician assistant, nurse practitioner, or other medically or non-medically trained service provider who may provide information, service or support to the patient.

The system may include a mapping module 24. The term "module" may refer to a hardware based module, software based module or a module may be a combination of hardware and software resources. A module (whether hardware, software, or a combination thereof) may be designed to implement or execute one or more particular functions, tasks or routines of the system. Embodiments of hardware based modules may include self-contained components such as chipsets, specialized circuitry and one or more memory devices. A software-based module may be part of a program code or linked to program code containing specific programmed instructions loaded in a memory device.

Figure 6:
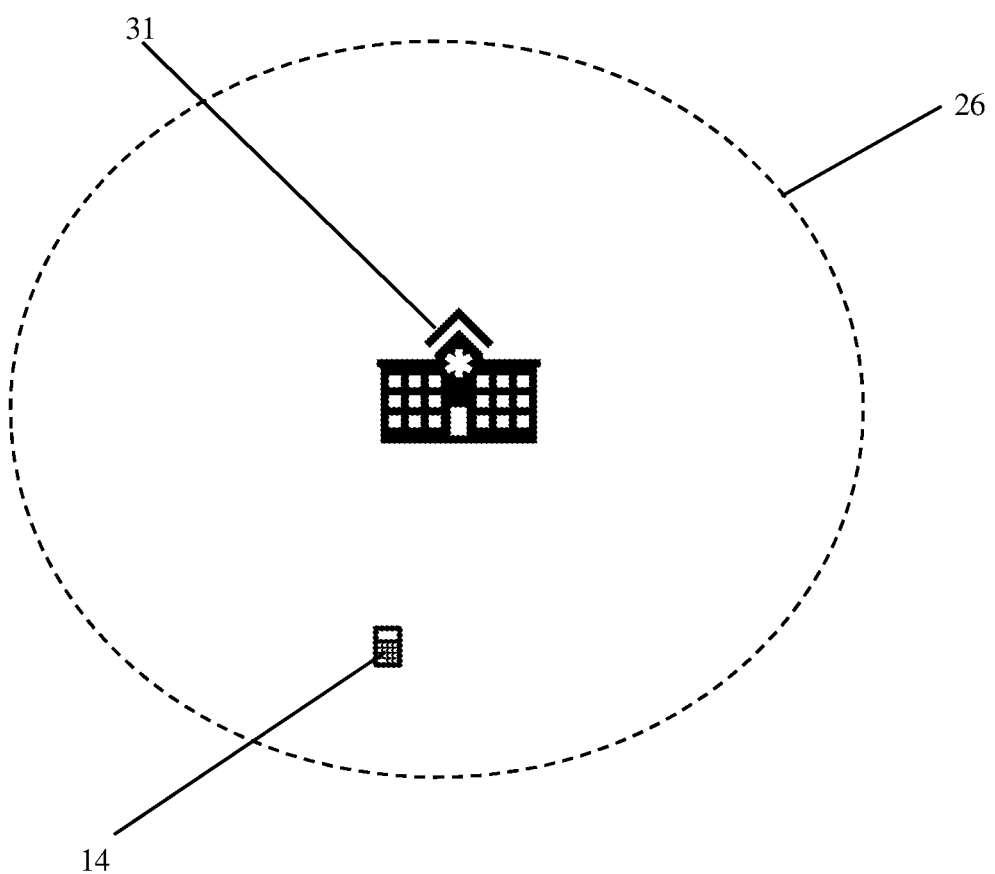
FIG. 6 is a schematic view of a healthcare facility surrounded by a geofence area associated with a healthcare facility and illustrating a mobile device located within the geofenced area according to the present invention.
Figure 7:
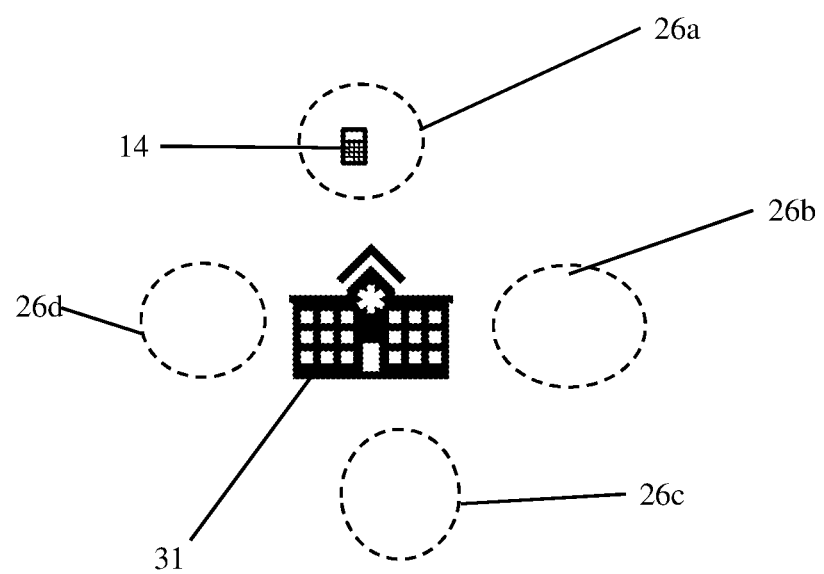
FIG. 7 is a schematic view of a healthcare facility with a first group of geofenced areas associated with a healthcare facility and illustrating a mobile device located within one of the geofenced areas according to the present invention.

The mapping module 24 may create one or more geofenced areas such as one geofenced area 26 (FIG. 6) associated with a healthcare facility based on data in the system. The mapping module 24 may create a first group of geofenced areas 26a-26d (FIG. 7) based on data in the system. The first group of geofenced areas 26a-26d may be created to correspond to or associate with the healthcare facility 31 as shown in FIG. 7. Each geofenced area of the first group may be entered from directions or ways that differ from each of the other one or more geofenced areas in the first group of geofenced areas 26a-26d. For example, an emergency room on a hospital campus may have several geofenced areas associated with it, since one large geofenced area encircling the emergency room would not work, because there may be too many false triggers for people going to the hospital for other purposes. Further, there may be cases where there are one or more parking lots, driveways or entrances that are exclusively for the emergency room, so these parking lots and other such location would be associated with a geofenced area for the emergency room. This would also allow for an earlier detection and notification compared with just having a small geofenced area around the emergency room.

The mapping module 24 may receive geofence configuration data defining the properties of each geofenced area. The geofence configuration data may include data defining each geofences' name, location, and size or virtual boundary limits (i.e. longitude, latitude and radius). The geofencing configured may comprise a defined geographic boundary area (a radius around an address, geo position coordinates, or other specified location or a geometric boundary such as a geofence or a proximity (distance) from a specific location.

The mapping module 24 may create interruption conditions based on data in the system 10 to prevent outputting messages to the client device 14 when the location data of the client device 14 is determined to be within a geofenced area. This avoids unnecessary triggers from emergency rooms, urgent cares or walk-in clinics and may be based on information about where a patient or person associated with the client device 14 works, lives, and/or where or when his or her daily activities (e.g. commuting, shopping, walking, running, bike-riding, etc.) are performed. This information may come from his or her addresses (home, work, gym, etc.) stored in a data store 30, as well as from location data from his or her client device 14. For example, an interruption condition may be created for the workplace of a person associated with the client device 14 and activated only during the working hours of the person if the workplace is a healthcare facility. A person may operate the computer 12 to enter the data to create the interruption condition. The interruption conditions may be based on one or more predetermined dates and times when the location data of the mobile device is determined to be within the geofenced area. The interruption conditions may also be based on determining that the patient frequently passes through the geofenced area en route to another location. The interruption conditions may also be based on determining that the patient frequents the geofenced area for purposes unrelated to receiving medical care.

The system 10 may include a messaging system 32. The messaging system 32 may perform the functions, tasks and services of the system 10 directed toward creating notifications or messages and notification events associated with the system such as notifications to the client device 14. The message system may send a one or more notifications upon the occurrence of one or more of the programmed transitions. For example, when a client device 14 breaches a virtual boundary of a geofenced area (entering or exiting), a geofence notification may be transmitted to the client device 14.

Figure 2:
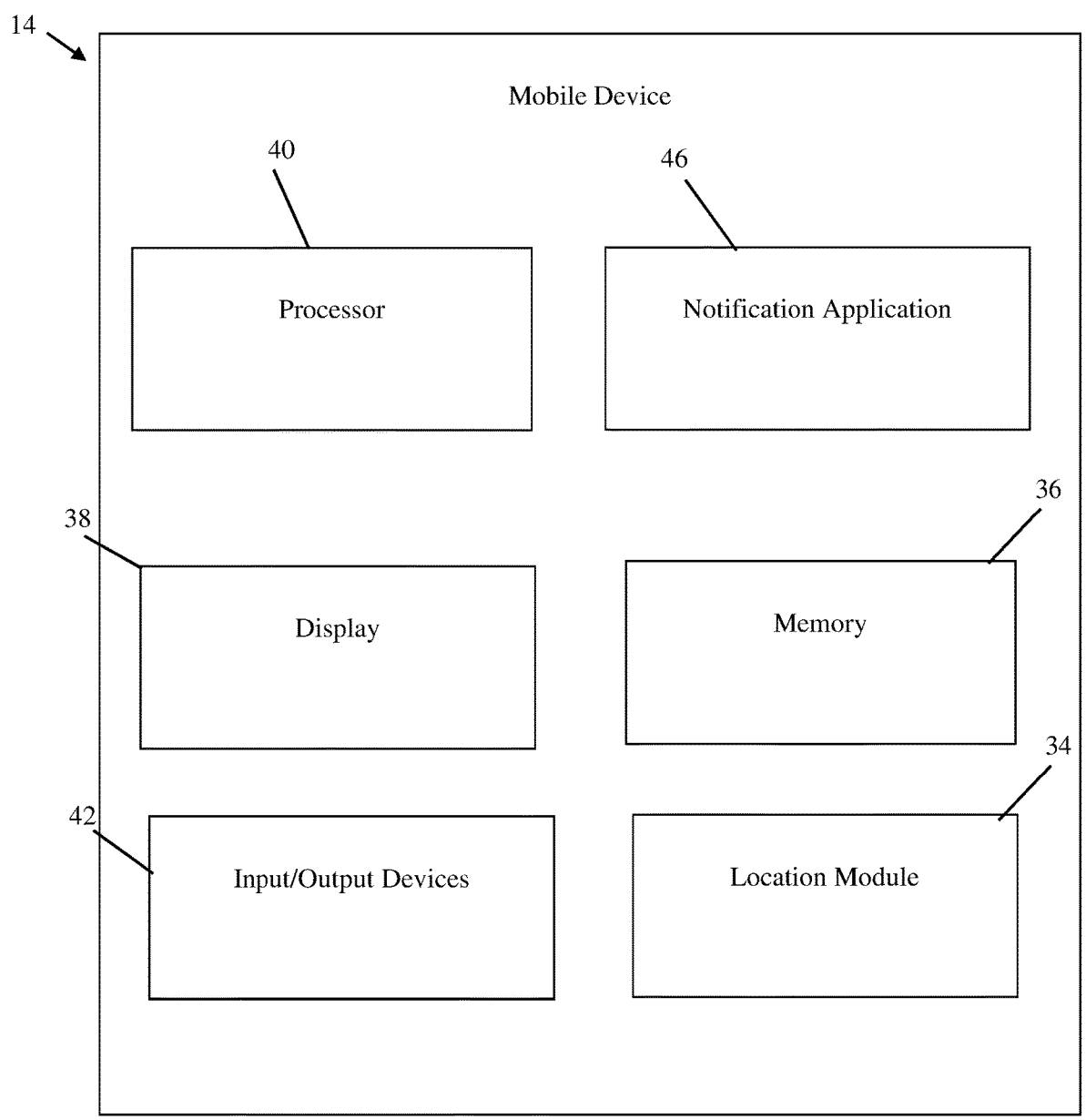
FIG. 2 is a block diagram of the client device and related elements according to the system of FIG. 1.

The system 10 may further comprise a location module 34 associated with the client device 14 as illustrated in FIG. 2. The location module 34 detects, processes and communicates the location of the client device associated with the user. Location sensing technology may include but is limited to global positioning systems (GPS), Wi-Fi, Bluetooth, 3G, 4G, 5G, 6G, 7G cellular technology, near field communications, radio frequency identification (RFID), beacons, and any other location identifying signal. The location module 34 may be comprised of hardware and/or software capable of utilizing a positioning system to pinpoint the current location of the client device 14 and/or previously stored locations of the client device 14 that may be saved in a memory device 36 or data store 30. The location module 34 may include a transmitter, receiver and/or transceiver for receiving location data from a positioning system or broadcasting the location data to the system 10. The location module 34 may save, store and update one or more sets of location data to a memory device onboard the location module 34 or, the location module 34 may store the location information to the memory device 36 or the data store 30. The location module 34 may include any sort of system that informs the mobile device of its geolocation including, but not limited to, the Global Positioning System of satellites circling the Earth.

With continued reference to FIG. 2, the client device 14 may be a portable device such as a mobile device in operative communication with each other. The mobile device 14 may be any computing device small enough to hold and operate in the hand. The mobile device 14 may comprise a display 38 having LCD flat screen interface that provides a touchscreen interface with digital buttons and keyboard, and/or physical buttons along with a physical keyboard. The mobile device 14 may connect to the Internet and interconnect with other devices such as car entertainment systems or headsets via Wi-Fi, Bluetooth, cellular networks or near field communication (NFC). The mobile device 14 may be a cell phone, smart phone, smart watch, tablet, PDA, laptop, notebook or other suitable portable or mobile device. The mobile device 14 is configured to detect its location and hence the location of a user using the mobile device 14 or other person near the mobile device 14.

The mobile device 14 includes one or more processors 40 and the memory device 36. The memory device 36 may contain a user identification module that may in turn contain a user identifier and/or user information. The user identifier may be a unique number or code that uniquely identifies the user of the mobile device. The mobile device 14 may also include input/output devices 42 such as a camera capable of taking still or video pictures and have the capability to make video calls (see FIG. 5). An antenna in the mobile device may send and receive wireless signals from sources such as the radio antenna and satellite. The antenna may, in some implementations, communicate directly with the server such as by exchanging wireless signals. The mobile device 14 may further comprise other input/output devices 42, such as a microphone and a speaker used, for example, in an implementation in which the mobile device 14 functions as a telephone. In some implementations, the mobile device 14 may also include a calendar/clock and a network interface. The calendar/clock may calculate time, date, and other data that can be derived from time data and date data.

The mobile device 14 includes applications that manage interactions between a server 44 (FIG. 1) and the mobile device 14. The applications may include a notification application 46. The data store 30 associated with the system 10 may contain data on healthcare facilities and their type. For example, the type of healthcare facility stored in the data store 30 may be a hospital, free-standing emergency, urgent care, or walk-in clinic. One or more of the healthcare facilities stored in the data store 30 may be associated with the patient associated with the mobile device 14. For example, the healthcare facility may be in the patient's insurance network with this data stored in the data store 30.

The data store 30 may also store personal and medical information about the patient in the form of a record. This and other information may be made available to the patient or other person via the mobile device 14 or computer 12. The data store 30 may store an address associated with a property and a geofenced area associated with the property. The data store 30 also may store all the mobile phone numbers of the smartphones which have the notification application 46 installed. The installed notification application 46 has the geofence information so that the mobile device 14 knows, using GPS technology, whether it is inside or outside the geofenced area.

The data store 30 may store information on patient(s) or person(s) associated with the mobile device related to their medical history to speed the process of receiving the services of the healthcare facility, lists of medical questions to ask, ratings on the facility being entered or the medical professionals practicing at that facility, information about whether the facility and\or medical providers participate in their insurance network, the medical providers practicing at the healthcare facility, wait times at the healthcare facility, and the proximity to other healthcare facilities and information about the prices of the facility or providers. This data may be displayed on the display 38 of the mobile device 14. The data store 30 may store the interruption conditions for preventing the outputting of the notification when the location data of the mobile device is determined to be within the geofenced area that are created using the mapping module 24 in exemplary embodiments.

Figure 4:
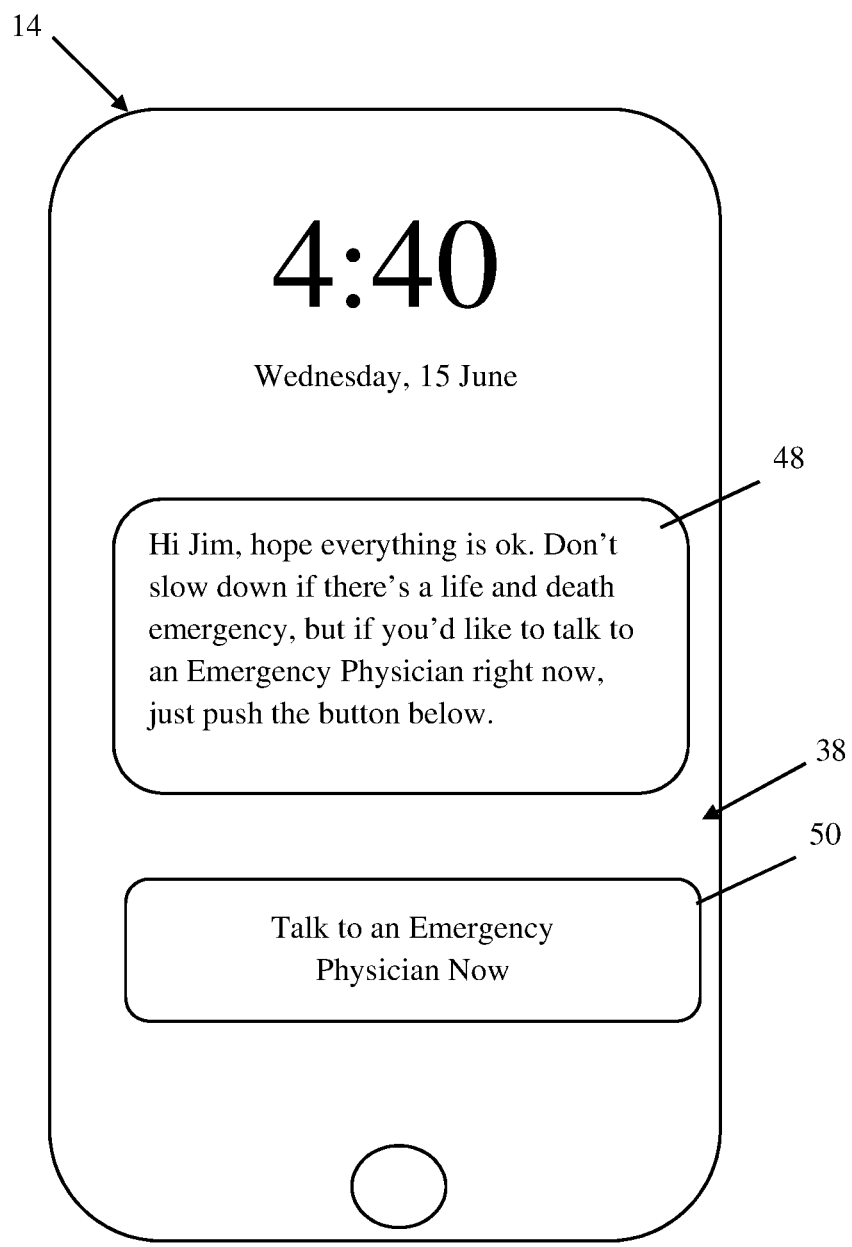
FIG. 4 is a schematic front view of mobile device displaying a message and message button on the display of the mobile device of the system according to FIG. 1.

The system 10 may identify a type of healthcare facility and then map or link that type with a certain message. The message may include a button. For example, an emergency healthcare facility may be linked with a notification or message 48 and a message button 50 for making video calls displayed on the display 38 of the mobile device 14 as shown in FIG. 4. The computer 12 may display on its display 20a the above-mentioned information corresponding to the healthcare facilities or the patient associated with the client device or other information for the medical professional to access.

The computer 12 and mobile device 14 may communicate with the server 44 via the internet over the network 16 as illustrated in FIG. 1. The network may include any one or combination of multiple different types of networks, such as cable networks, local area networks, personal area networks, wide area networks, the Internet, wireless networks, ad hoc networks, mesh networks, and/or the like. In some implementations the satellite and/or the radio antenna may provide network connectivity to the mobile device as well as provide geolocation. For example, the radio antenna may provide network access to the mobile device according to the International Mobile Telecommunications-2000 standards (3G network) or the International Mobile Telecommunications Advanced standards (4G network) or the 5G or 6G networks. Other implementations may include one source of geolocation data such as the satellite and a separate source of network connectivity such as a Wi-Fi hotspot. The server may house or otherwise have a connection to multiple data stores including user information and/or other data stores. The server 44 and data stores can be stored where desired, for example in a cloud.

Generally, the user information contains information about the user associated with the mobile device 14. The notification application 46 is operatively connected to the server 44 which is connected to the data store 30. The notification application 46 has notifications and messages associated with different types of conditions. The messages may include buttons for the user to operate. For example, FIG. 4 shows a notification message 48 and message button 50 for making video calls generated by the messaging system 32 when the mobile device 14 enters a geofenced area associated with a free-standing emergency facility. The notifications or messages may be stored in the memory 36 of the mobile device 14 or in the data store 30. One or more notifications may include information about one of or any combination of: the medical history of the patient, the type of healthcare facility associated with the geofenced area, the insurance network of the patient, the medical providers practicing at the healthcare facility, wait times at the healthcare facility, and the proximity to other healthcare facilities. The notification may further include an invitation or suggestion to initiate a video or audio call to a qualified person that can help the patient regarding the unscheduled visit. Alternatively, or in addition, the first notification may include a voice message that may include the above-mentioned information.

Figure 3:
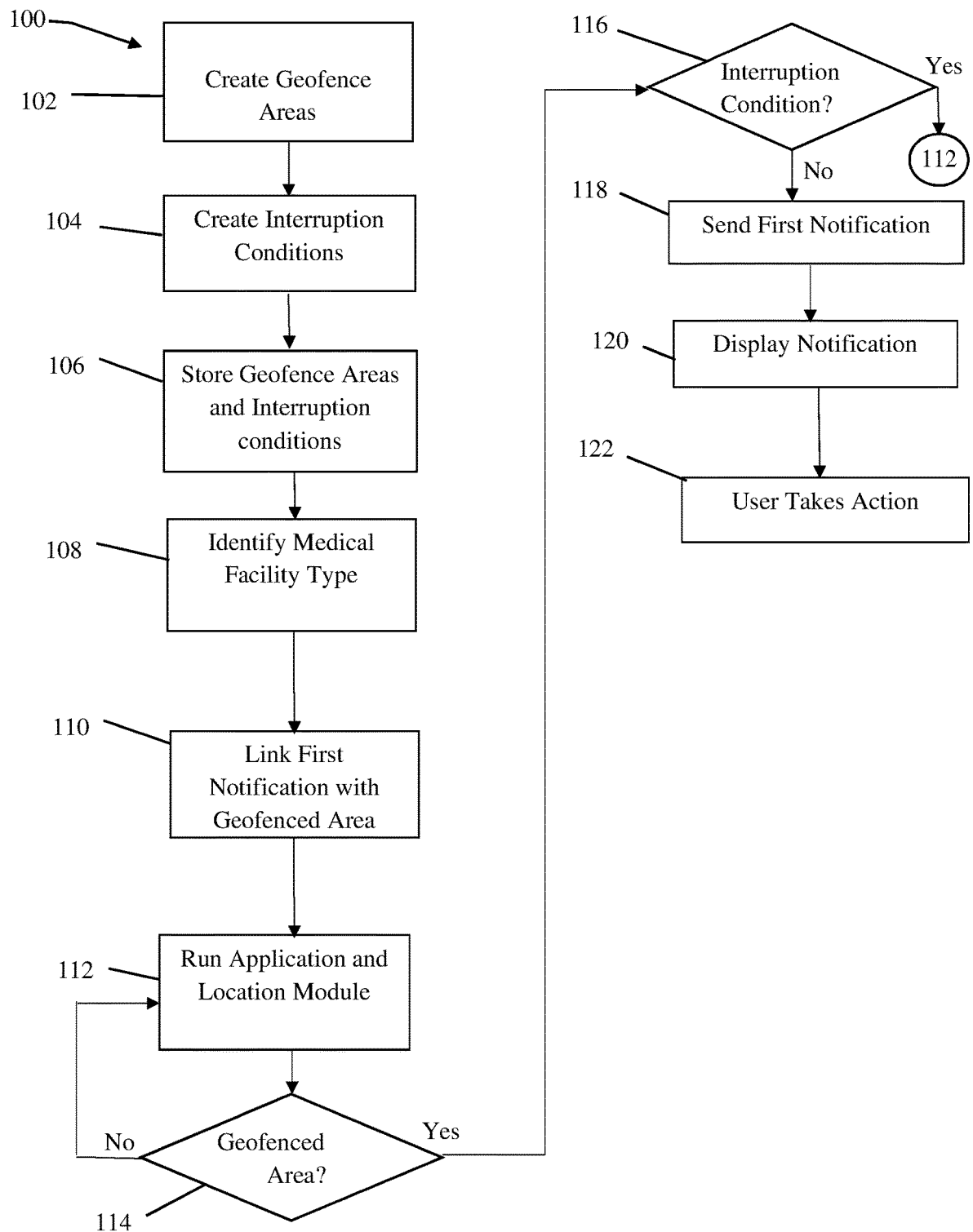
FIG. 3 is a flow diagram of an exemplary method according to FIG. 1.

With reference now to FIG. 3, an example methodology 100 is illustrated and described. While the methodology is described as being a series of acts or steps that are performed in a sequence, it is to be understood that the methodology is not limited by the order of the sequence. For instance, some acts or steps may occur in a different order than what is described herein. In addition, a step may occur concurrently with another step. Furthermore, in some instances, not all steps may be required to implement a methodology described herein.

Moreover, the steps or acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodology may be stored in a computer-readable medium, displayed on the display device, and/or the like.

In each step of this sequence of client-server message exchanges, a computer may process a request and return data. In step 102, the geofenced areas are created using the mapping module 24 based on data in the data store 30. One or more of the geofenced areas created may correspond to a first healthcare facility 31. For example, one geofenced area 26 may be created for the first healthcare facility as shown in FIG. 6. In another example, a first group of geofenced areas 26a-26d may be created to correspond to the first healthcare facility as shown in FIG. 7. For example, an emergency room on a hospital campus may have several geofenced areas, since one large geofenced area encircling the emergency room would not work, because there may be too many false triggers for people going to the hospital for other purposes. Further, there may be cases where there are one or more parking lots, driveways or entrances that are exclusively for the emergency room, so these parking lots and other such location would be associated with a geofenced area for the emergency room. This would also allow for an earlier detection and notification compared with just having a small geofenced area around the emergency room.

In step 104, the interruption conditions for preventing the outputting of the notification when the location data of the mobile device is determined to be within the geofenced area may be created using the mapping module 24. In step 106, the geofenced areas and any interruption conditions are stored in the data store. In step 108, the first healthcare facility may be identified. For example, the healthcare facility stored may be identified as a hospital, free-standing emergency, urgent care, or walk-in clinic and other information related to that facility. In step 110, a first predetermined notification stored in the data store 30 or in the memory of the mobile device 14 may be linked with the one or more geofenced areas of the first healthcare facility. This notification may include messages with information about one of or any combination of the medical history of the patient, the type of healthcare facility associated with the geofenced area, the insurance network of the patient, the medical providers practicing at the healthcare facility, wait times at the healthcare facility, and the proximity to other healthcare facilities. The notification may further includes an invitation or suggestion to initiate a video or audio call to a qualified person that can help the patient regarding the unscheduled visit.

In step 112, the mobile device 14 is turned on with the notification application 46 launched and running and the location module 34 running so that the system 10 receives location data of the mobile device 14. In step 114 the notification application 46 determines when the mobile device 14 is located within a geofenced area associated with the first healthcare facility 31 stored in the data store 30. This may occur during an unscheduled visit to the healthcare facility by the patient. If the mobile device 14 is located within the geofenced area, then the system 10 may check in step 116 whether there is an interruption condition for that geofenced area. If there is an interruption condition, no notification is outputted to the mobile device 14 and the method goes back to step 112 to continue to receive location data of the mobile device 14.

Figure 5:
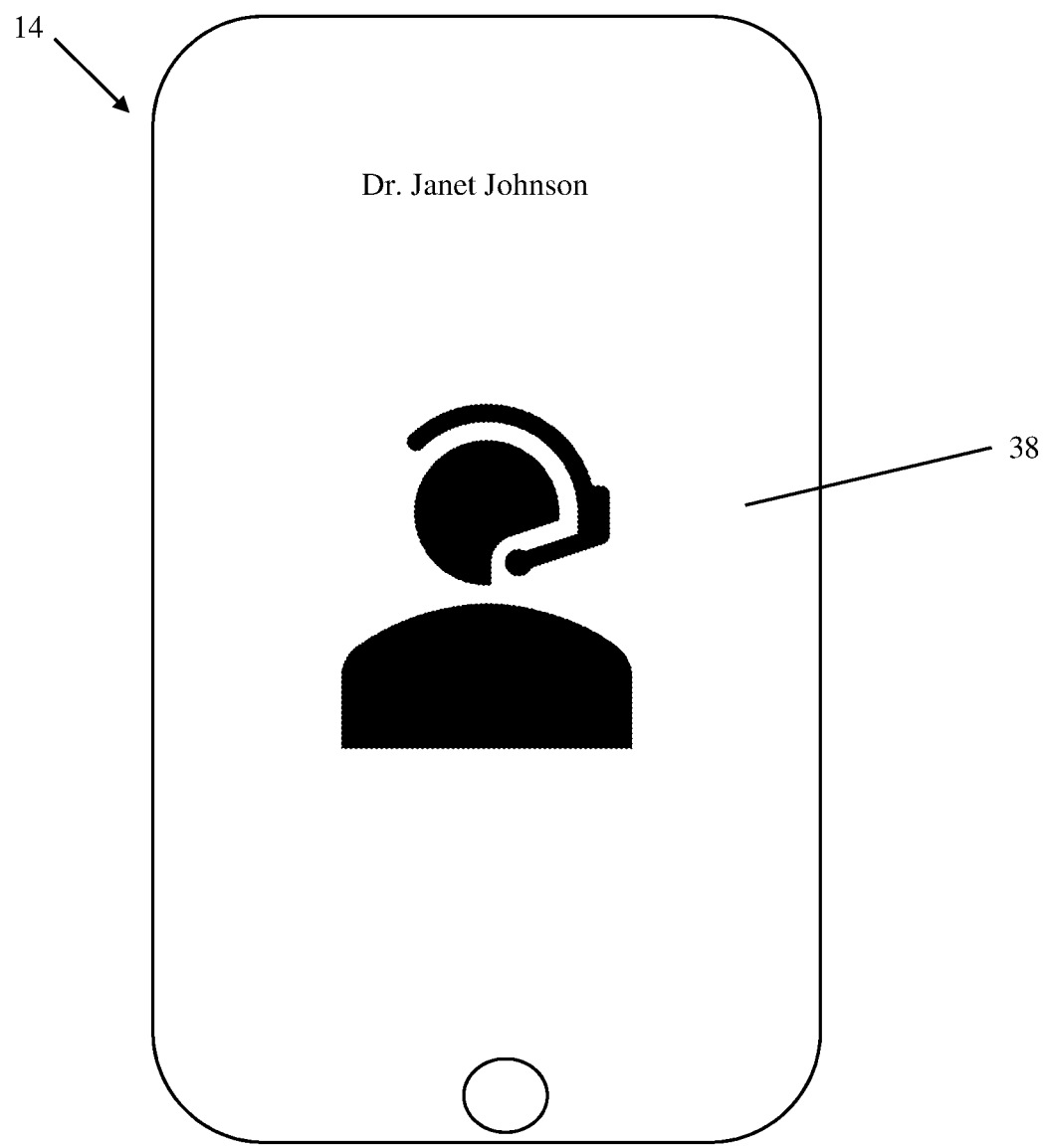
FIG. 5 is a schematic front view of mobile device displaying an image of a video call initiated by the user on the mobile device of the system according to FIG. 1.

If the mobile device 14 is located within the geofenced area and there is no interruption condition, then in step 118, the messaging system 32 sends the first predetermined notification to the mobile device 14 or the predetermined notification is retrieved from the memory of the mobile device 14. In step 120, the notification is displayed on the display 38 of the mobile device 14. The notification may include a message button 50 to give the option to place an audio or video call with a qualified healthcare professional an invitation or suggestion to initiate a video or audio call to a qualified person that can help the patient regarding the unscheduled visit. Alternatively or in addition, other ways to output the message may be provided such as an audio message outputted through the speakers of the mobile device. In step 122, the user may take action based on the displayed message(s). For example, FIG. 4 shows a notification message and a message button generated by the messaging system 32 when the mobile device 14 enters the first geofenced area 26a associated with a free-standing emergency facility. If the user presses the message button 50 on the display 38, a video call will be placed with a doctor or other qualified professional that can help the patient regarding the unscheduled visit as illustrated in FIG. 5. The medical professional may be a doctor, physician assistant, nurse practitioner, or other medically or non-medically trained service provider who may provide information, service or support to the patient and can help the patient regarding the unscheduled visit. The method may also include enabling the user to cancel the notification without placing the call or taking further action.

In one example, a video call may be placed with a doctor to determine whether or not the injury requires going to an emergency medical facility. For certain injuries, the doctor may ask the patient to take a photograph of the injury using the mobile device and send the photograph to the doctor by email, text, or other suitable mode. Upon analyzing the photograph, the doctor may determine that the injury does not require the services of an emergency healthcare facility. The doctor may operate the computer to search the data store 30 and find an urgent care facility near the patient's location based on the mobile phone location and then suggest to the patient to go to the less costly urgent care facility, since the injury does not require use of an emergency healthcare facility.

The system and method provides information quickly and conveniently to patients who seek immediate medical attention when they are approaching a healthcare facility and also to the medical professions involved with the patient, which also saves costs and time to diagnose and treat the medial condition of the patient and process the medical information. Although various embodiments of the disclosed system and method for providing notifications to a user based upon the user's location have been shown and described, modifications may occur to those skilled in the art upon reading the specification. The present application includes such modifications and is limited only by the scope of the claims.

What is claimed is:

1. A computer-implemented method for providing notifications and communication based on a patient entering into a geofenced area around a healthcare services facility for an unscheduled visit, the method comprising the following operations performed by at least one computer processor:
   a) creating a geofenced area associated with a mobile device and a location that has the healthcare facility, wherein the patient is associated with the mobile device;
   b) storing the geofenced area in a data store;
   c) determining when the mobile device has crossed or entered the geofenced area during the unscheduled visit to the healthcare facility by the patient;
   d) sending a notification to or retrieving the notification from the mobile device, wherein the notification includes information about one of or any combination of: the medical history of the patient, the type of healthcare facility associated with the geofenced area, the insurance network of the patient, the medical providers practicing at the healthcare facility, wait times at the healthcare facility, and the proximity to other healthcare facilities, wherein the notification further includes an invitation or suggestion to initiate a video or audio call to a qualified person that can help the patient regarding the unscheduled visit; and
   e) outputting the notification to the mobile device when the location data of the mobile device is determined to be within the geofenced area that corresponds to the healthcare facility.

2. The computer-implemented method of claim 1, wherein the notification includes an invitation or suggestion to initiate a video or audio call by displaying a button on a display of the mobile device to be pressed for initiating the video or audio call to the qualified person that can help the patient regarding the unscheduled visit upon pressing the button.

3. The computer-implemented method of claim 2, wherein information corresponding to the healthcare facility or patient associated with the mobile device or both is displayed on a computer accessed by the qualified person upon the video or audio call being initiated.

4. The computer-implemented method of claim 3, wherein the information includes at least one of or any combination of a medical history of a patient or a family member associated with the mobile device, recommended lists of questions to ask personnel of the healthcare facility, ratings on the healthcare facility being entered, information about the medical professionals practicing at the healthcare facility, information about whether the healthcare facility or medical providers participate in the insurance network of the patient or family member associated with the mobile device, and information about the prices of the healthcare facility or medical providers.

5. The computer-implemented method of claim 2, wherein the qualified person includes a doctor, physician assistant, nurse practitioner, or other medically or non-medically trained service provider who may provide information, service or support to the patient.

6. The computer-implemented method of claim 1, further comprising enabling a person to cancel the notification without taking further action.

7. The computer-implemented method of claim 1, wherein the notification includes information about a medical history of a patient or a family member associated with the mobile device, recommended lists of questions to ask personnel of the healthcare facility, ratings on the healthcare facility being entered, information about the medical professionals practicing at the healthcare facility, information about whether the healthcare facility or medical providers participate in the insurance network of the patient or family member associated with the mobile device, and information about the prices of the healthcare facility or medical providers.

8. The computer-implemented method of claim 1, further comprising preventing the outputting of the notification based on one or more predetermined dates and times when the location data of the mobile device is determined to be within the geofenced area.

9. The computer-implemented method of claim 1, further comprising preventing the outputting of the notification based on determining that the patient frequents the geofenced area for purposes unrelated to receiving medical care.

10. The computer-implemented method of claim 1, further comprising preventing the outputting of the notification based on determining that the patient frequently passes through the geofenced area en route to another location.

11. The computer-implemented method of claim 1, wherein the healthcare facility includes one of or any combination of a hospital, free-standing emergency room, urgent care center, walk-in clinic, and facility that a person can attend for unscheduled care.

12. The computer-implemented method of claim 1, wherein the notification includes information on the medical history of the patient, the type of healthcare facility associated with the geofenced area, the insurance network of the patient, the medical providers practicing at the healthcare facility, wait times at the healthcare facility, and the proximity to other healthcare facilities.

13. A computer-implemented method for providing notifications, the method comprising the following operations performed by at least one computer processor:
   a) creating a group of geofenced areas, wherein the group of geofenced areas are associated with a mobile device and a location that has a healthcare facility, wherein a patient is associated with the mobile device;
   b) storing the geofenced areas in a data store;
   c) determining when the mobile device has crossed or entered at least one of the geofenced areas in the group of geofenced areas;
   d) sending a notification to or retrieving the notification from the mobile device, wherein the notification includes information about one of or any combination of the medical history of the patient, the type of healthcare facility associated with the geofenced area, the insurance network of the patient, the medical providers practicing at the healthcare facility, wait times at the healthcare facility, and the proximity to other healthcare facilities, wherein the notification includes an invitation or suggestion to initiate a video or audio call by displaying a button on a display of the mobile device to be pressed for initiating the video or audio call to a qualified person that can help the patient upon pressing the button; and e) outputting the notification to the mobile device when the location data of the mobile device is determined to be within the at least one geofenced area that corresponds to the healthcare facility.

14. The computer-implemented method of claim 13, wherein each geofenced area may be entered from directions or ways that differ from the each of the other one or more geofenced areas in the first group of geofenced areas.

15. The computer-implemented method of claim 13, wherein information corresponding to the healthcare facility or patient associated with the mobile device or both is displayed on a computer accessed by the qualified person upon the video or audio call being initiated.

16. The computer-implemented method of claim 13, further comprising preventing the outputting of the notification based on one or more predetermined dates and times when the location data of the mobile device is determined to be within the geofenced area.

17. The computer-implemented method of claim 13, further comprising enabling a person to cancel the notification without taking further action.

18. A non-transitory computer-readable storage medium storing executable instructions that, as a result of being executed by one or more processors of a computer system, cause the computer system to at least:

a) create a geofenced area associated with a mobile device and a location that has the healthcare facility, wherein the patient is associated with the mobile device;

b) store the geofenced area in a data store;

c) determine when the mobile device has crossed or entered the geofenced area during the unscheduled visit to the healthcare facility by the patient;

d) send a notification to or retrieving the notification from the mobile device, wherein the notification includes information about one of or any combination of: the medical history of the patient, the type of healthcare facility associated with the geofenced area, the insurance network of the patient, the medical providers practicing at the healthcare facility, wait times at the healthcare facility, and the proximity to other healthcare facilities, wherein the notification further includes an invitation or suggestion to initiate a video or audio call to a qualified person that can help the patient regarding the unscheduled visit; and e) output the notification to the mobile device when the location data of the mobile device is determined to be within the geofenced area that corresponds to the healthcare facility.

19. The non-transitory computer-readable storage medium of claim 18, wherein the notification includes an invitation or suggestion to initiate a video or audio call by displaying a button on a display of the mobile device to be pressed for initiating the video or audio call to the qualified person that can help the patient regarding the unscheduled visit upon pressing the button.

20. The non-transitory computer-readable storage medium of claim 18 wherein the instructions further including instructions that, as a result of being executed by one or more processors, cause the computer system to:

prevent the output of the notification based on one or more predetermined dates and times when the location data of the mobile device is determined to be within the geofenced area.

* * * * *